United States Patent [19]

Hu

[11] Patent Number: 4,685,654

[45] Date of Patent: Aug. 11, 1987

[54] FLOW REGULATOR FOR DRIP INFUSION

[76] Inventor: Liang-Tung Hu, 3F., No. 248, Sec. 4, Sinyi Rd., Taipei, Taiwan

[21] Appl. No.: 1,816

[22] Filed: Jan. 8, 1987

[51] Int. Cl.⁴ ........................... F16K 7/16; F15C 3/04
[52] U.S. Cl. ..................................... 251/205; 138/46; 604/246; 604/248
[58] Field of Search ................. 251/4, 8, 205; 138/45, 138/46; 604/246, 248, 249, 250, 256

[56] References Cited

U.S. PATENT DOCUMENTS

| | | | |
|---|---|---|---|
| 2,992,808 | 7/1961 | Burritt, Jr. et al. | 251/205 |
| 3,294,360 | 12/1966 | Lunberg | 251/205 |
| 3,900,184 | 8/1975 | Burke et al. | 251/6 |
| 4,300,552 | 11/1981 | Cannon | 251/4 |
| 4,552,336 | 11/1985 | Pastrone | 251/205 |

FOREIGN PATENT DOCUMENTS

30452  7/1926  France .................................... 251/8

Primary Examiner—George L. Walton
Attorney, Agent, or Firm—James E. Eakin

[57] ABSTRACT

A flow regulator for drip infusion, comprising a rigid main body in which a rigid flow path is integrally formed. The flow path is substantially omega-shaped, and has a V-shaped cross section in its middle section, of which the upper side is open and closed by a flexible disc which has a ridge extending perpendicular to the flow path and can be pressed to change the effective size of an orifice formed between the ridge and the V-shaped flow path, thereby allowing for a stable control of the flow rate.

4 Claims, 12 Drawing Figures

FLOW REGULATOR FOR DRIP INFUSION

The present invention relates to a flow regulator for drip infusion.

Figure 7:
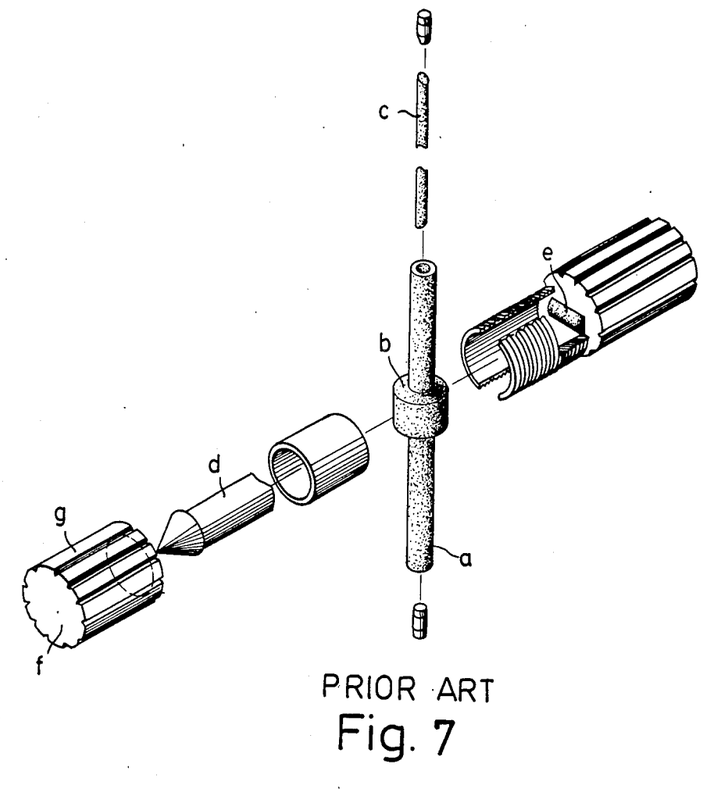
FIG. 7 is a fragmentary view of a known flow regulator.

In a previous invention by the same inventor, U.S. Pat. No. 4,575,041, a flow regulator for drip infusion was disclosed. FIG. 7 shows a fragmentary view of such a flow regulator. It comprises a rubber hose (a), the two ends of which are respectively connected upstream to a hose from the dripping bottle and downstream to a hose leading to an injecting needle. The portion where the rubber hose (a) is squeezed is provided with a rubber ring (b) to ensure a better squeezing. By squeezing the rubber ring to change the sectional area of the rubber hose, the dripping rate can be controlled. A rubber rod (c) is retained in the squeezed portion of the rubber hose (a) to obtain a more accurate and stable flow rate.

The squeezing action is achieved by a metal plunger (d) which urges the rubber ring (b) against a ridge (e). The ridge must extend in a direction perpendicular to the rubber hose (5) to achieve a maximal control. The plunger (d) is driven by turing a knob (f) to produce an axial thrust to press the rubber ring (b). Co-rotation of plunger with the knob (f) must be avoided, since any torsion exerted by the plunger (d) on the rubber ring (6) may cause serious wear after a long period of use. For this reason, the plunger (d) has a conical end to give a pointwise contact with the knob (f). The knob (f) is provided with parallel ribs (g) to increase its friction to facilitate the fingers to turn the knob.

In use, this flow regulator proves far more advantageous than a conventional gear clamp. However, such a flow regulator is still not perfectly satisfactory. Its structure is a bit too complicated. The rubber hose (a) and rubber ring (b) are all flexible parts, therefore lacking a rigid support, so that the accuracy of dripping rate may be affected by the movement of the patient. Moreover, since the rubber rod (c) is not fixed, but floatingly retained in the rubber hose (a), there is the risk that the rubber rod may drift downstream away from the rubber hose (5). Moreover, the knob lacks retaining means to retain it in its mounting. In every use, a nurse must loosen the knob to drive away the air bubbles in the hose. If the knob is unscrewed too much, it may fall out from its mounting.

Accordingly, it is an object of the present invention to provide an improved flow regulator to obviate the aforesaid disadvantages.

According to the present invention, the flow path is integrally formed in a rigid body, and the flow rate is controlled by squeezing a flexible disc received in the rigid body. In so doing, the flow path becomes "rigid", as opposed to the "flexible" flow path of its predecessors, and is therefore unaffected by the movement of the patient.

Another aspect of this invention is that it provides an ideal flow path which allows for better control of the dripping flow. The squeezing portion has a V-shaped cross section, and the flow path sinuates vertically in the rigid body to define an omega-shaped (or oxbow-shaped) "meander". This meander achieves a stabilization equivalent to the rubber rod (c) in the prior art.

According to a further aspect of this invention, there is provided a retaining means which prevents the knob from falling out because of excessive unscrewing.

The present invention will be better understood when read in connection with the accompanying drawing, in which:

DETAILED DESCRIPTION OF PREFERRED EMBODIMENT

Figure 1:
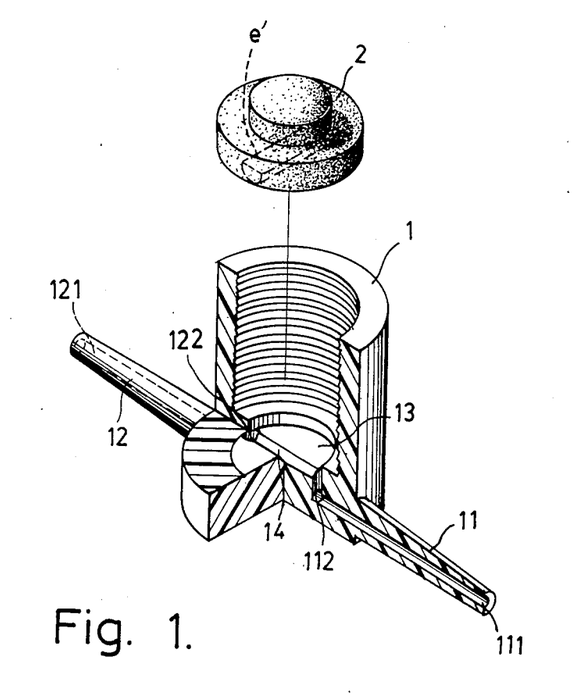
FIG. 1 is a perspective sectional view of the main body and flexible disc according to a first embodiment of this invention.

With reference to FIG. 1, it can be seen that the main body (1) is a hollow, rigid cylinder with two diametrically opposite projections (11 and 12) for connecting with the upstream hose and downstream hose. The cylinder is closed at its lower end and its bottom (13) is situated at a level slightly higher than the canals (111 and 121) in projections (11 and 12). A groove (14) with V-shaped section is formed on the bottom (13) and two vertical holes (112 and 122) are provided at both ends of groove (14) to communicate the groove (14) with the two canals (111 and 121). Thus an omega-shaped meander is formed by (111),(112), (14), (122), and (121). The upper side of groove (14) is open, and should be closed by a flexible disc (2) made of rubber material. The bottom side of flexible disc (2) is provided with an integral ridge (e'). Here the ridge (e') must be flexible, since the flow path is rigid. In the prior art, ridge (e) is not necessarily rigid, since its flow path is flexible. When the disc (2) is placed in position, the ridge (e') is perpendicular to groove (14). When the disc (2) is pressed, part of the ridge (e') is pushed into the groove (14) to partially or totally block the groove (14), thus the dripping rate can be controlled. From experimental data, it can be seen that the V-shaped cross section is by far the best shape to give a constant flow rate, and the omega-shaped meander can further enhance the stability of the flow. As stated hereinbefore, an ideal control can be achieved when the ridge is perpendicular to the flow path which is to be squeezed by the ridge. Accordingly, a constant, steady, and finely adjustable dripping can be achieved using the present invention.

Figure 2:
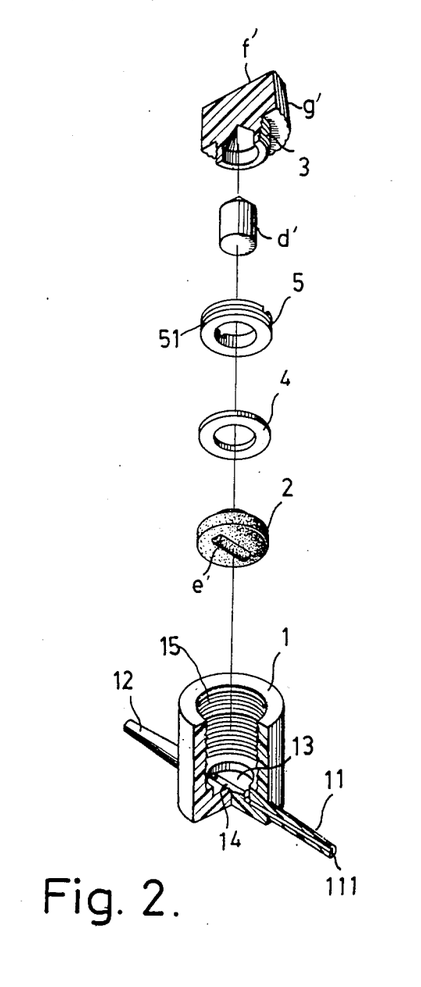
FIG. 2 is a fragmentary view of the first embodiment of the this invention.

The squeezing of disc (2) is similar to the prior art. FIG. 2 shows a first embodiment of this invention. A plunger (d') is driven by a knob (f') to press the flexible disc (2) against bottom (13), thereby changing the effective sectional area of groove (14) to regulate the flow rate. The knob (f') is provided with external threads (3) at its lower end which engages with the internal threads (15) of main body (1). When knob (f') is turned in the forward direction, an axial thrust is produced and disc (2) is pressed against bottom (13). On the other hand, when knob (f') is turned in the reverse direction, disc (2) is released, and its elasticity will push plunger (d') upward. Like the prior art, knob (f') is provided with parallel ribs (g'). Since the upper side of groove (14) is open and only closed by disc (2), in order to ensure the watertightness of this device, a bushing (20) and a threaded ring (5) are provided to sealingly retain disc (2) in place. Threaded ring (5) is externally provided with thread (51) to engage with internal thread (15) of main body. This is a known sealing technique, and hence a detailed description herein is not necessary.

Figure 3:
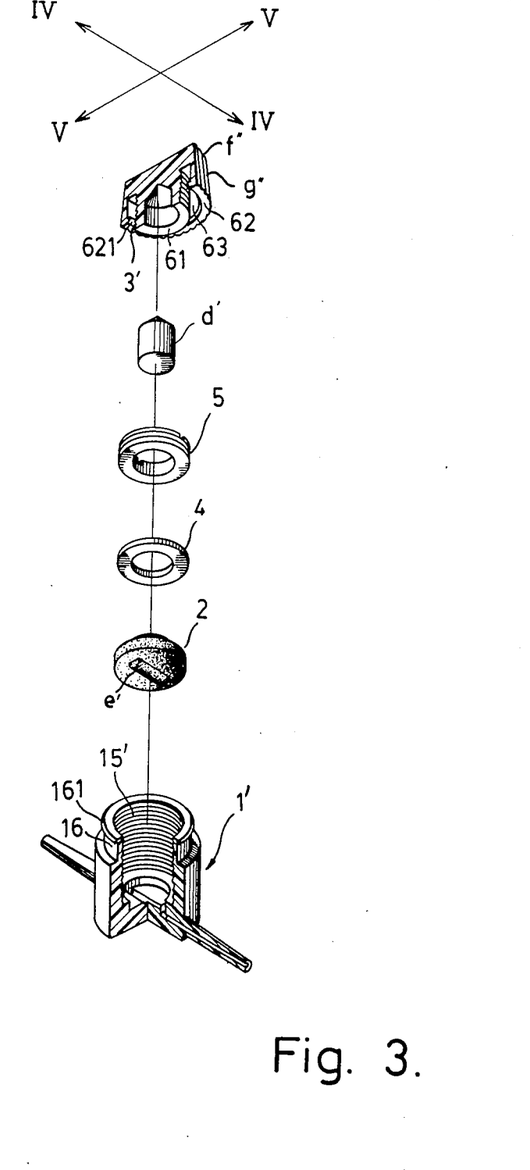
FIG. 3 is a fragmentary view of a second embodiment of this invention.
Figure 4A:
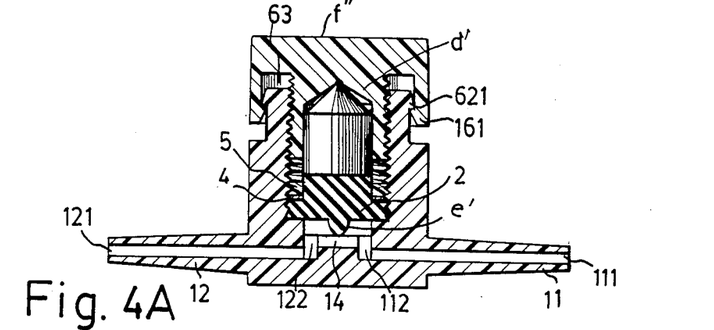
FIGS. 4A to 4C are sectional views of the second embodiment along line IV—IV in FIG. 3, respectively showing the regulator in fully open, half open, and closed conditions.
Figure 4B:
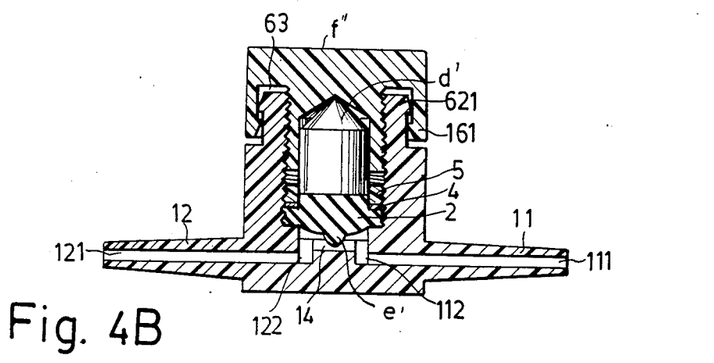
Figure 4C:
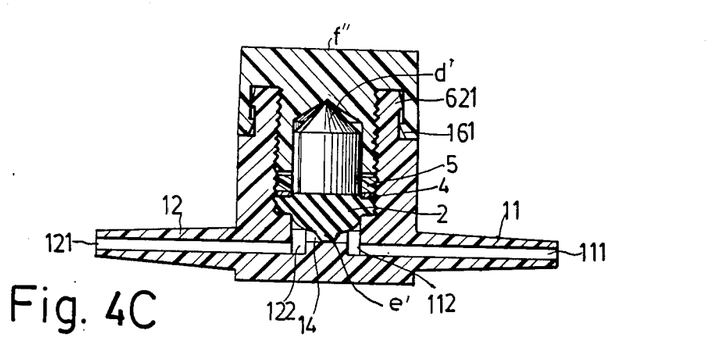
Figure 5A:
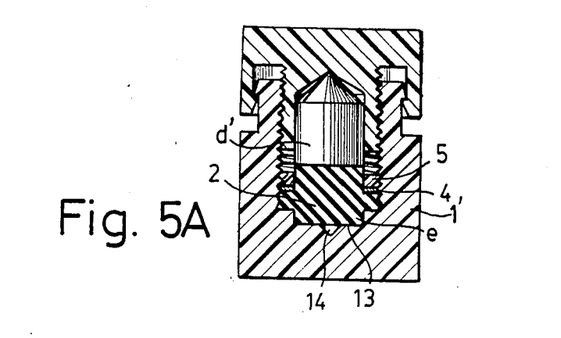
FIGS. 5A to 5C are the sectional views along line V—V in FIG. 3, respectively corresponding to FIGS. 4A to 4C.
Figure 5B:
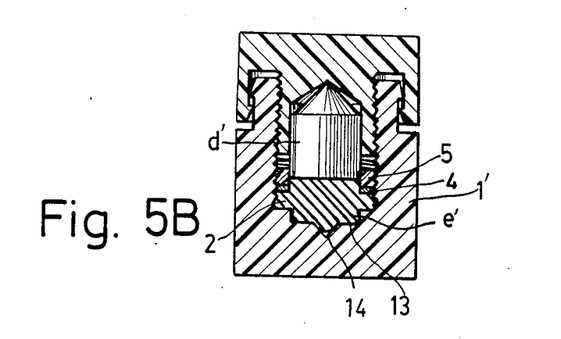
Figure 5C:
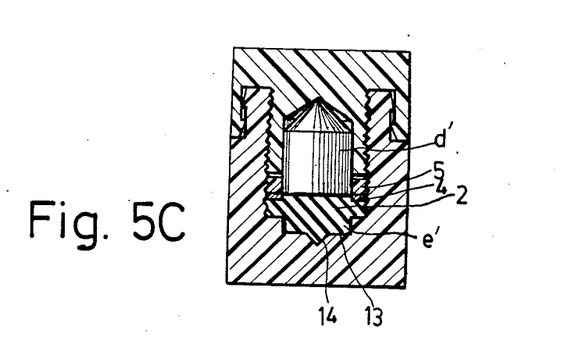

In the first embodiment, there is no retaining means to retain the knob (f') on the main body (1) to prevent it from falling out by excessive turning in reverse direction. Though special retaining means can be attached to main body (1) and knob (f') to prevent knob (f') from falling out, the best method of retention is illustrated in the embodiment shown in FIG. 3. Here the upper end (16) of main body (1') has a smaller outer diameter, with a small flange (161) formed around its margin. The knob (f''), has an inner portion (61) provided with external threads (3') and an outer portion (62) externally provided with ribs (g''). Between the inner portion (61) and the outer portion (62) there is an annular space (63) to receive the upper end (61) of main body. The external thread (3') can engage with the internal thread (15') to convert an angular rotation into an axial thrust. The inner lower margin of outer portion (62) is provided with an internal flange (621). The external diameter of external flange (161) slightly outsizes the inner diameter of inner flange (621). In assemblage, the knob (f'') can be pushed onto the upper end (16) of main body (1'). Because of the resilience of the material of the knob (f'') and the main body (1'), the external flange (161) can resiliently pass over the internal flange (621) and enter the recess (63) in which it is retained permanently from then on. In so doing, the knob (f'') is free from the risk of falling out by excessive reverse rotation.

Having thus described the two variants of the present invention, the detailed description in operation is further illustrated in FIGS. 4A to 4C and FIGS. 5A to 5C.

In a fully opened state (see FIG. 4A and 5A), the ridge (e') rests on bottom 13, leaving a V-shaped orifice in the middle part of groove (14). When the knob is turned in a forward direction, the flexible disc (2) is pressed by plunger (d') and deformed, and the V-shaped orifice is partially occupied by the deformed ridge (e'), and the flow rate is reduced. (See FIG. 4B and FIG. 5B) When the knob is further turned forwardly so that plunger (d') reaches its "lower dead point" (see FIG. 4C and FIG. 5C), the V-shaped orifice is fully filled by the more severely deformed ridge (e') and the flow is totally cut off.

Figure 6:
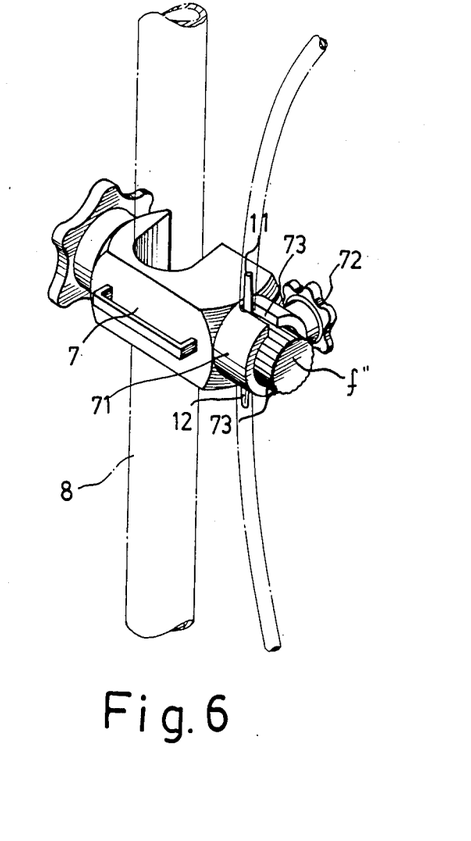
FIG. 6 is a perspective view showing the present invention in its mounting on a drip infusion stand.

In actual use, the flow regulator can be supported on a holder (7) which is adjustably fastened on the shaft (8) of an infusion set stand (not shown). The holder has a cylindrical receiver (71) to receive the main body (1) therein within fastening means (72) to secure it in place. The receiver (71) is provided with two diametrically opposite slits (73) running along its length to facilitate the flow regulator to be mounted into or dismounted from the receiver (71).

Figure 8:
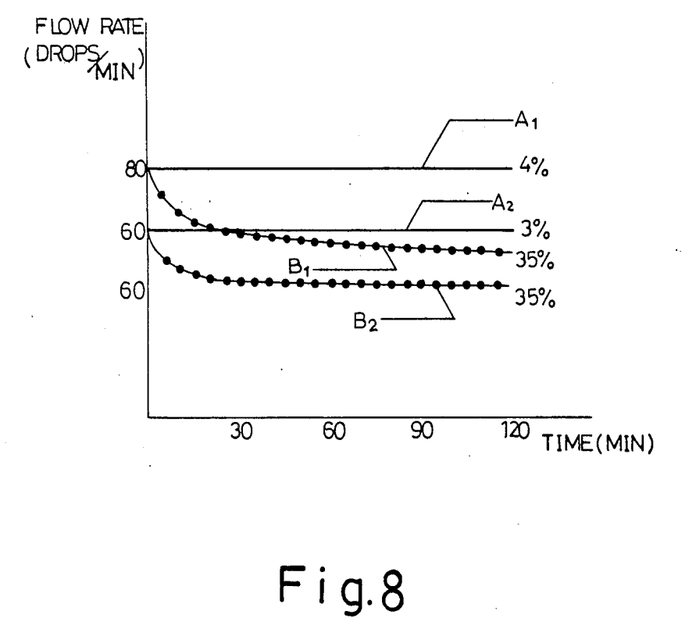
FIG. 8 is a graph illustrating the difference between the present invention and conventional regulating clamps.

FIG. 8 illustrates the difference of flow rates between the present invention and the conventional regulating clamp. Here lines A1, A2 respectively represent the present invention with two initial conditions, whereas curves B1 and B2 respectively represent the conventional clamp with two initial conditions. It is evident that the results of the present invention are far stabler than the conventional regulating clamps.

I claim:

1. A flow regulator for drip infusion comprising a flow path with both ends respectively connected to an upstream hose coming from a dripping infusion set and to a downstream hose leading to an injecting needle, and flow regulating means which varies the effective flowing section of said flow path to control the flow rate of the liquid flowing through the regulator by actuating means for acting on pressing means to press a ridge against said flow path, said ridge extending perpendicular to said flow path, said actuating means producing a pressing action by a hollow threaded knob with an open end and a closed end, in which there is provided a plunger which has a pointed end contacting with the inner side of the closed end of said knob and a flat end pointing towards said flow path, said plunger being perpendicular to said flow path and said ridge, said flow regulating means being such that the rotation of said knob can produce a torsionless axial thrust from said plunger toward said flow path, said flow regulator being characterized by a rigid main body in form of a hollow cylinder with an open upper end and a closed lower end with two diametrically opposite projections near the lower end thereof, each of said projections being internally provided with a canal and being open at the distal ends thereof to respectively connect with an upstream hose and a downstream hose, the lower closed end of said main body having a flat inner bottom at a level slightly higher than said two canals, said bottom being provided with a groove with a V-shaped cross section, said groove extending in the direction of said projections, each of the ends of said groove being provided with a hole extending in the axial direction of said main body to respectively communicate with the proximal end of each of said canals and being contiguous, thereby defining an omega-shaped flow path, said pressing means being a flexible disc received in said main body between said flat inner bottom and said plunger and being substantially equal to the diameter of the interior of the main body, said ridge being flexible and integrally formed on one side of said flexible disc and having a length substantially equal thereto and being perpendicularly deformed into said groove, the other side of said flexible disc opposite to said ridge being in direct contact with the flat end of said plunger to allow said actuating means to deform said ridge within said groove to regulate the flow rate through said flow path.

2. The flow regulator according to claim 1, wherein said main body is provided with fastening means to sealingly fasten said flexible disc in said main body.

3. The flow regulator according to claim 1, wherein said main body is internally threaded.

4. The flow regulator according to claim 1, further comprising retaining means to fixedly retain said knob on the open end of said main body.

* * * * *